United States Patent
Pak et al.

(10) Patent No.: US 10,874,321 B2
(45) Date of Patent: Dec. 29, 2020

(54) PHASE SINGULARITY IDENTIFICATION SYSTEM AND METHOD

(71) Applicant: INDUSTRY-ACADEMIC COOPERATION FOUNDATION YONSEI UNIVERSITY, Seoul (KR)

(72) Inventors: Hui Nam Pak, Seoul (KR); Jun Seop Song, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 233 days.

(21) Appl. No.: 16/078,795

(22) PCT Filed: Feb. 22, 2017

(86) PCT No.: PCT/KR2017/001943
§ 371 (c)(1),
(2) Date: Oct. 19, 2018

(87) PCT Pub. No.: WO2017/146459
PCT Pub. Date: Aug. 31, 2017

(65) Prior Publication Data
US 2019/0046063 A1 Feb. 14, 2019

(30) Foreign Application Priority Data
Feb. 23, 2016 (KR) ........................ 10-2016-0021346

(51) Int. Cl.
*A61B 5/0452* (2006.01)
*A61B 5/04* (2006.01)
(Continued)

(52) U.S. Cl.
CPC ............ *A61B 5/0452* (2013.01); *A61B 5/042* (2013.01); *A61B 5/046* (2013.01); *A61B 5/04012* (2013.01); *A61B 5/4836* (2013.01)

(58) Field of Classification Search
CPC ... A61B 5/0452; A61B 5/04012; A61B 5/042; A61B 5/046; A61B 5/4836
(Continued)

(56) References Cited

U.S. PATENT DOCUMENTS

| 2013/0006131 A1* | 1/2013 | Narayan | A61B 5/4839 |
| | | | 600/508 |
| 2014/0088395 A1* | 3/2014 | Dubois | A61B 5/046 |
| | | | 600/382 |
| 2015/0313491 A1* | 11/2015 | Edwards | A61B 5/0422 |
| | | | 600/374 |

FOREIGN PATENT DOCUMENTS

| JP | 2012-523281 A | 10/2012 |
| JP | 2012-524606 A | 10/2012 |

(Continued)

OTHER PUBLICATIONS

Iyer et al. "An Experimentalist's Approach to Accurate Localization of Phase Singularities during Reentry", Biomedical Engineering Society, 2001, vol. 29(1), pp. 47-59 (Year: 2001).*

(Continued)

*Primary Examiner* — Erin M Piateski
(74) *Attorney, Agent, or Firm* — LRK Patent Law Firm

(57) ABSTRACT

A phase singularity identification system includes: a signal reception unit for receiving a single activity electrogram signal measured through a single-electrode catheter at a particular point of a cardiac muscle cell; a phase calculation unit for calculating a phase from the received single activity electrogram signal; and a phase singularity identification unit for identifying through the calculated phase if the particular point of the cardiac muscle cell is a phase singularity. Accordingly, it is possible to identify the phase singularity of a rotor by using a single-electrode catheter rather than a multi-electrode catheter, thereby significantly reducing time required and costs spent in comparison with prior art, and it is possible to accurately identify the phase singularity of the rotor, thus the system can be used for a radiofrequency electrode catheter ablation procedure for cardiac arrhythmia treatment.

15 Claims, 5 Drawing Sheets

(51) Int. Cl.
  *A61B 5/042* (2006.01)
  *A61B 5/00* (2006.01)
  *A61B 5/046* (2006.01)

(58) Field of Classification Search
  USPC ........................................................ 600/509
  See application file for complete search history.

(56) References Cited

FOREIGN PATENT DOCUMENTS

JP     2012-228378 A    11/2012
KR     10-1443156 B1    9/2014

OTHER PUBLICATIONS

Search Report, dated May 15, 2017, for International Application No. PCT/KR2017/001943.
Written Opinion, dated May 15, 2017, for International Application No. PCT/KR2017/001943.
Anand N. Iyer et al., "An Experimentalist's Approach to Accurate Localization of Phase Singularities during Reentry", Bimedical Engineering Society, 2001, vol. 29(1), pp. 47-59.
JPO Office Action dated Oct. 23, 2019 for Japanese Patent Application No. 2018-544565 which corresponds to the above-identified U.S. application.
Young-Seon Lee et al., "A New Efficient Method for Detecting Phase Singularity in Cardiac Fibrillation", PLoS One, Dec. 1, 2016, 11(12):e0167567, 1/14-14/14, doi:10.1371/journal.phone.0167567.

\* cited by examiner

PHASE SINGULARITY IDENTIFICATION SYSTEM AND METHOD

CROSS-REFERENCE TO RELATED APPLICATIONS

The present application is a U.S. National Phase entry from International Application No. PCT/KR2017/001943, filed Feb. 22, 2017, which claims priority to Korean Patent Application No. 10-2016-0021346, filed Feb. 23, 2016, the disclosures of which are incorporated by reference herein in their entireties.

BACKGROUND OF THE INVENTION

1. Technical Field

The present invention relates to a system and method for identifying a phase singularity and, more particularly, to a system and method capable of identifying whether a particular point of a cardiac muscle cell is a phase singularity based on a single activity electrogram signal.

2. Description of Related Art

Arrhythmias are a symptom in which a cardiac activation map becomes abnormal to speed up, slow down or make irregular a cardiac impulse. Atrial fibrillation of such arrhythmias is one of the most common types. The mechanism of atrial fibrillation has not been clarified although the possibility of ischemic stroke and an untimely death is very high, and treatment therefor is also not easy. As one mechanism for maintaining atrial fibrillation for atrial fibrillation treatment, there is a rotor, that is, the center of an electric pulse whirlwind. However, the rotor has a problem in that research and clinic application of the rotor are not easy because the detection of the rotor is not easy.

The rotor for atrial fibrillation treatment is mathematically defined as the phase singularity of an electrical pulse. A method of identifying a phase singularity was first proposed by Iyer and Gray, "An Experimentalist's Approach to Accurate Localization of Phase Singularities during Reentry", Annals of Biomedical Engineering 29(1), 2001.

The thesis is a kind of conventional technology. All of phases at the respective locations of a heart tissue are calculated, and a phase singularity is detected by detecting that the phases continuously make one rotation.

In the conventional technology, however, electrical conduction mapping through the simultaneous recording of a multi-electrode catheter must be performed in order to identify whether a specific point is a phase singularity. Accordingly, there are problems in that the time taken to identify a phase singularity increases and a cost consumed therefor increases. The present invention proposes a system and method capable of significantly reducing the time taken to identify a phase singularity and a cost consumed therefor compared to a conventional technology.

SUMMARY OF THE INVENTION

An object of the present invention is to propose a system and method for capable of significantly reducing time and costs in determining a phase singularity of a rotor.

Meanwhile, technical objects to be achieved by the present invention are not limited to the aforementioned object, and various technical objects may be derived within the range evident to those skilled in the art from the following description.

A system for identifying a phase singularity according to an embodiment of the present invention includes a signal reception unit receiving a single activity electrogram signal ($x[n]$, n is a natural number) measured through a single electrode catheter at a particular point of a cardiac muscle cell, a phase calculation unit calculating a phase ($\theta[n]$, n is a natural number) from the single activity electrogram signal received by the signal reception unit, and a phase singularity identification unit identifying whether the particular point of the cardiac muscle cell is a phase singularity based on the phase calculated by the phase calculation unit. The present invention has advantages in that it can significantly reduce the time and a consumed cost compared to a conventional technology by identifying a phase singularity of a rotor using a single electrode catheter not a multi-electrode catheter and the present invention can be used for a high-frequency electrode catheter ablation procedure for cardiac arrhythmia treatment by precisely identifying a phase singularity of a rotor.

Furthermore, the phase calculation unit may calculate the phase from the single activity electrogram signal according to Equation 1 $\theta[n]=\arctan 2\ (x[n+\tau]-k, x[n]-k)$ (wherein $\theta[n]$ is the phase, $x[n]$ is the single activity electrogram signal, $\tau$ is a delay constant, and k is a base value of the single activity electrogram signal)

Moreover, in the phase calculated by the phase calculation unit, an electrical state of the cardiac muscle cell may appear as values $-\pi$ to $\pi$. The phase calculation unit may calculate the phase up to $\theta[n+1]$.

Furthermore, the phase singularity identification unit identifies that the particular point of the cardiac muscle cell is a phase singularity when n satisfying Equation 3 $\theta[n+1]-\theta[n]\leq-M$ (wherein M is a phase singularity identification condition and is a specific constant) is present. M, that is, the phase singularity identification condition, may be $\pi$.

Meanwhile, the system for identifying a phase singularity according to an embodiment of the present invention may be implemented as a method of identifying a phase singularity, which includes the steps of (a) receiving, by a signal reception unit, a single activity electrogram signal ($x[n]$, n is a natural number) measured through a single electrode catheter at a particular point of a cardiac muscle cell, (b) calculating, by a phase calculation unit, a phase ($\theta[n]$, n is a natural number) from the single activity electrogram signal received by the signal reception unit, and (c) identifying, by a phase singularity identification unit, whether the particular point of the cardiac muscle cell is a phase singularity based on the phase calculated by the phase calculation unit and is another embodiment capable of implementing the same technical characteristic.

In this case, the step (b) may include calculating the phase from the single activity electrogram signal according to Equation 1 $\theta[n]=\arctan 2\ (x[n+\tau]-k, x[n]-k)$ (wherein $\theta[n]$ is the phase, $x[n]$ is the single activity electrogram signal, $\tau$ is a delay constant, and k is a base value of the single activity electrogram signal)

Furthermore, in the phase calculated in the step (b), an electrical state of the cardiac muscle cell may appear as values $-\pi$ to $\pi$. The step (b) may further include the step (b-1) of calculating, by the phase calculation unit, a phase $\theta[n+1]$ according to the equation.

Moreover, the step (c) may include (c-1) identifying that the particular point of the cardiac muscle cell is a phase singularity when n satisfying Equation 3 $\theta[n+1]-\theta[n]\leq-M$ (wherein M is a phase singularity identification condition and is a specific constant) is present. The M may be π.

Finally, the method of identifying a phase singularity according to another embodiment of the present invention may be implemented as a program stored in a medium for executing the method in a computer.

Advantageous Effects

The present invention has an advantage in that it can significantly reduce a consumed time and cost compared to a conventional technology by identifying a phase singularity of a rotor using a single electrode catheter not a multi-electrode catheter.

Furthermore, the present invention has an advantage in that it can be used for a high-frequency electrode catheter ablation procedure for cardiac arrhythmia treatment by precisely identifying a phase singularity of a rotor.

Meanwhile, effects of the present invention are not limited to the aforementioned effects, and may include various other effects within the range evident to those skilled in the art from the following description.

DETAILED DESCRIPTION OF THE INVENTION

Figure 1:
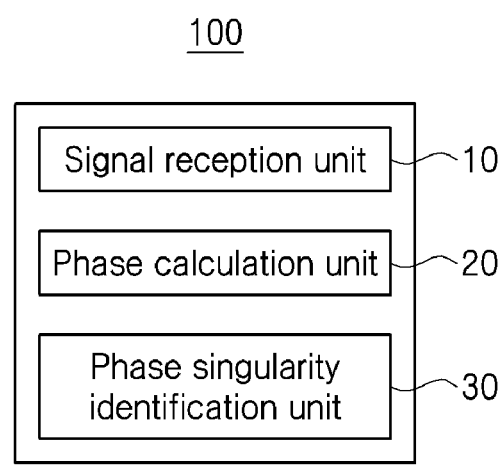
FIG. 1 is a diagram showing a general configuration of a system for identifying a phase singularity according to an embodiment of the present invention.

Hereinafter, some embodiments of the present invention are described in detail with reference to the exemplary drawings. The embodiments are provided so that those skilled in the art may easily understand the technological spirit of the present invention and the present invention is not restricted by the embodiments. A detailed description of the known functions and constructions will be omitted if it is deemed to make the gist of the present invention unnecessarily vague.

Furthermore, contents represented in the accompanying drawings have been diagrammed in order to easily describe the embodiments of the present invention, and may be different from forms that are actually implemented. It is to be noted that in assigning reference numerals to elements in the drawings, the same reference numerals denote the same elements throughout the drawings even in cases where the elements are shown in different drawings.

Furthermore, it should be understood that an expression that some elements are "included" is an expression of an "open type" and the expression simply denotes that the corresponding elements are present, but does not exclude additional elements.

FIG. 1 is a diagram showing a general configuration of a system 100 for identifying a phase singularity according to an embodiment of the present invention.

The system 100 for identifying a phase singularity includes a signal reception unit 10, a phase calculation unit 20 and a phase singularity identification unit 30, but this is only an embodiment. Some elements may be added or deleted, if necessary.

Figure 2:
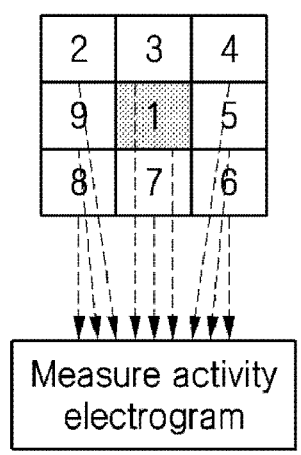
FIG. 2 is a diagram showing the state in which an activity electrogram at a particular point of a cardiac muscle cell is measured using a multi-electrode catheter that is a conventional technology.
Figure 3:
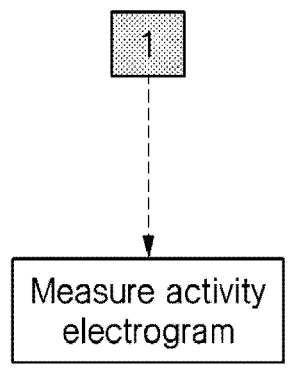
FIG. 3 is a diagram showing the state in which an activity electrogram at a particular point of a cardiac muscle cell is measured using a single electrode catheter according to an embodiment of the present invention.

The signal reception unit 10 receives a single activity electrogram signal (x[n], n is a natural number) measured through a single electrode catheter at a particular point of a cardiac muscle cell. In this case, a known electrode catheter used for a high-frequency electrode catheter ablation procedure may be used as the single electrode catheter. FIGS. 2 and 3 show a difference between the single electrode catheter and a conventional technology related to an electrode catheter. FIG. 2 is a diagram showing the state in which an activity electrogram at a particular point of a cardiac muscle cell is measured using a multi-electrode catheter that is a conventional technology. Referring to FIG. 2, in order to identify a phase singularity at a No. 1 point, all of activity electrograms for Nos. 2 to 9 points that surround the No. 1 point must be measured. In accordance with FIG. 3 that is an embodiment of the present invention, however, in order to identify a phase singularity at the No. 1 point, only the activity electrogram of the No. 1 point has only to be measured. Accordingly, a multi-electrode catheter as in a conventional technology is not necessary. Only one electrode catheter of a multi-electrode catheter may be used according to circumstances. Although only one electrode catheter of the multi-electrode catheter is used, the activity electrograms of points that surround a point for identifying a phase singularity do not need to be measured. Accordingly, the time taken to identify a phase singularity and a cost consumed therefor can be significantly reduced, compared to a conventional technology.

Figure 4:
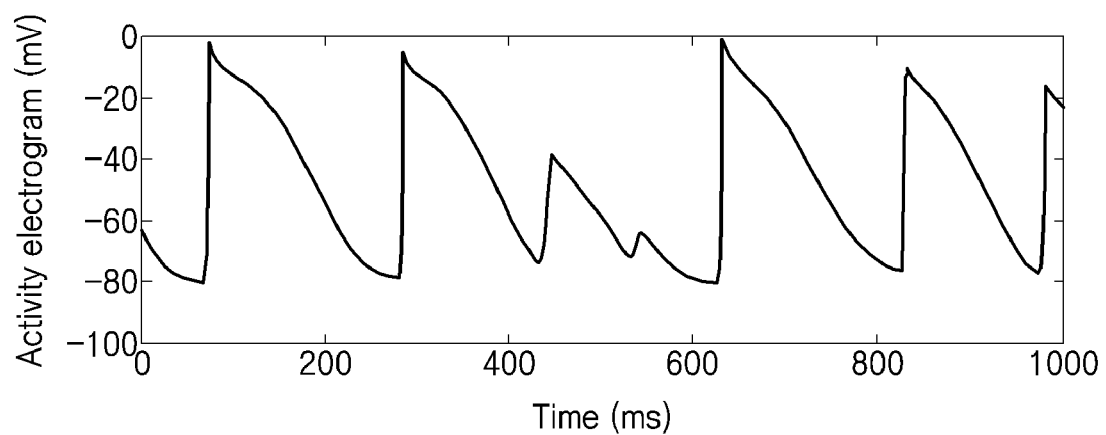
FIG. 4 is a diagram showing an example of a single activity electrogram signal received by a signal reception unit.

Meanwhile, an example of a single activity electrogram signal received by the signal reception unit 10 is shown in FIG. 4.

The phase calculation unit 20 calculates a phase (θ[n], n is a natural number) based on a single activity electrogram signal received by the signal reception unit 10. Specifically, the phase calculation unit 20 calculates the phase based on the single activity electrogram signal according to [Equation 1] below.

$$\theta[n]=\arctan 2(x[n+\tau]-k, x[n]-k) \quad \text{[Equation 1]}$$

In this case, θ[n] is the phase, and x[n] is the single activity electrogram signal. τ is a delay constant and may be set as a value corresponding a delay time, for example, 20 to 30 ms and may be freely adjusted by a system administrator. k is a base value of the single activity electrogram signal and may be set as the mean value of x[n] or a specific constant, for example, 0. Like the delay constant, k may be freely adjusted by a system administrator.

Figure 5:
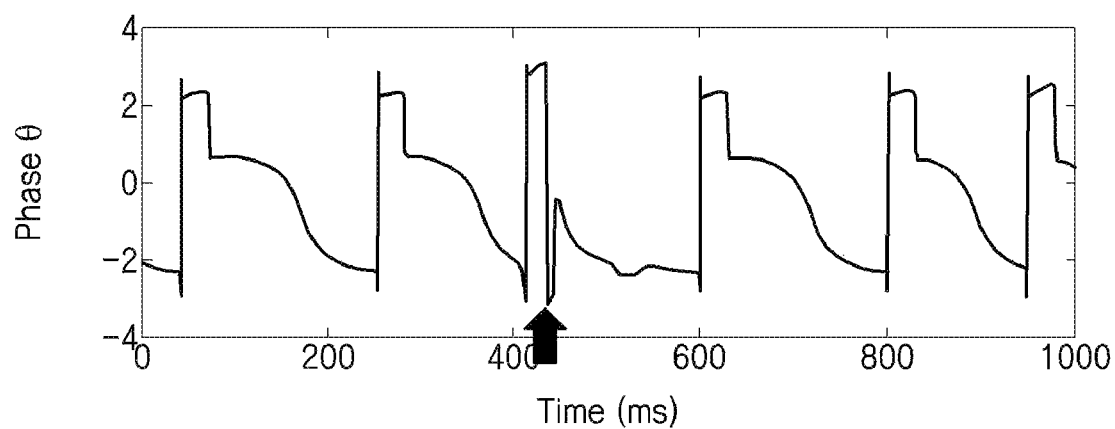
FIG. 5 is a diagram showing the state in which the single activity electrogram signal of FIG. 4 was calculated as a phase according to Equation 1.

Meanwhile, in the phase calculated according to [Equation 1], the electrical state of the cardiac muscle cell appears as values $-\pi$ to $+\pi$. From FIG. 5, it may be seen that single activity electrogram signals shown in FIG. 4 were calculated as phases according to [Equation 1].

The phase calculation unit 20 calculates a phase $\theta[n+1]$ in addition to the phase $\theta[n]$ of $x[n]$, that is, a single activity electrogram signal, in order to perform the phase identification function of the phase singularity identification unit 30. In this case, the phase calculation unit 20 may calculate the phase up to $\theta[n+1]$ according to [Equation 1]. A delay constant and a base value of the single activity electrogram signal need to be set in the same manner as the case where the phase $\theta[n]$ is calculated. [Equation 2] below may mean that the phase $\theta[n+1]$ is calculated according to [Equation 1].

$$\theta[n+1]=\arctan 2(x[n+1+\tau]-k, x[n+1]-k) \quad \text{[Equation 2]}$$

The phase singularity identification unit 30 identifies whether a particular point of a cardiac muscle cell is a phase singularity based on a phase calculated by the phase calculation unit 20. Specifically, the phase singularity identification unit 30 identifies whether a particular point of a cardiac muscle cell is a phase singularity according to [Equation 3] below.

$$\theta[n+1]-\theta[n] \leq -M \quad \text{[Equation 3]}$$

In this case, M is a phase singularity identification condition and is theoretically $2\pi$, but may be set as a specific constant, for example, a constant such as $\pi$ by taking into consideration elements, such as noise in the measurement of a single activity electrogram signal.

If n to satisfy [Equation 3] is present, the phase singularity identification unit 30 identifies that the particular point of the cardiac muscle cell is a phase singularity. This is based on a physical fact that the phase $\theta[n]$ is continuous function at all of points of the cardiac muscle cell except a phase singularity. Specifically, in accordance with the definition of a phase singularity, a value not 0 is calculated when $\theta[n]$ is integrated in a path that surrounds the periphery of a phase singularity. The reason for this is that $\theta[n]$ is not mathematically a continuous function well defined in a single connection region.

The system 100 for identifying a phase singularity, including the signal reception unit 10, the phase calculation unit 20 and the phase singularity identification unit 30, may identify whether a particular point of a cardiac muscle cell is a phase singularity by calculating a phase based on a single activity electrogram signal measured through a single electrode catheter. In this case, the phase singularity can be identified within a shorter time compared to a conventional technology because the activity electrograms of points to surround the particular point of the cardiac muscle cell are not measured. A consumed cost can be significantly reduced compared to a conventional technology because a single electrode catheter is used.

Figure 6:
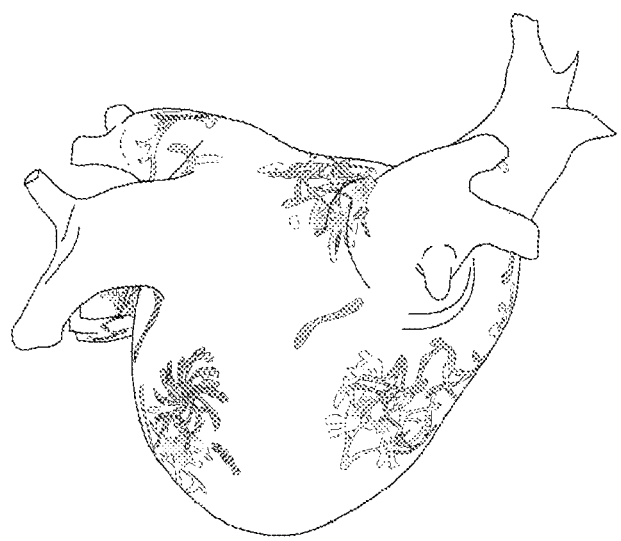
FIG. 6 is a diagram showing an anatomical image of a 3-D mapped heart for a phase singularity.

Furthermore, the system 100 for identifying a phase singularity according to an embodiment of the present invention may further include a mapping unit (not shown) capable of mapping an identified phase singularity on an anatomical image of the heart in a three-dimensional (3-d) manner. An anatomical image of the phase singularity mapped in a 3-D manner can be seen from FIG. 6. If a phase singularity is mapped to an anatomical image of the heart by the mapping unit (not shown), a high-frequency electrode catheter ablation procedure device may be connected to the system 100 for identifying a phase singularity. Accordingly, a mapped image can be received and easily used for a practical surgical procedure.

Figure 7:
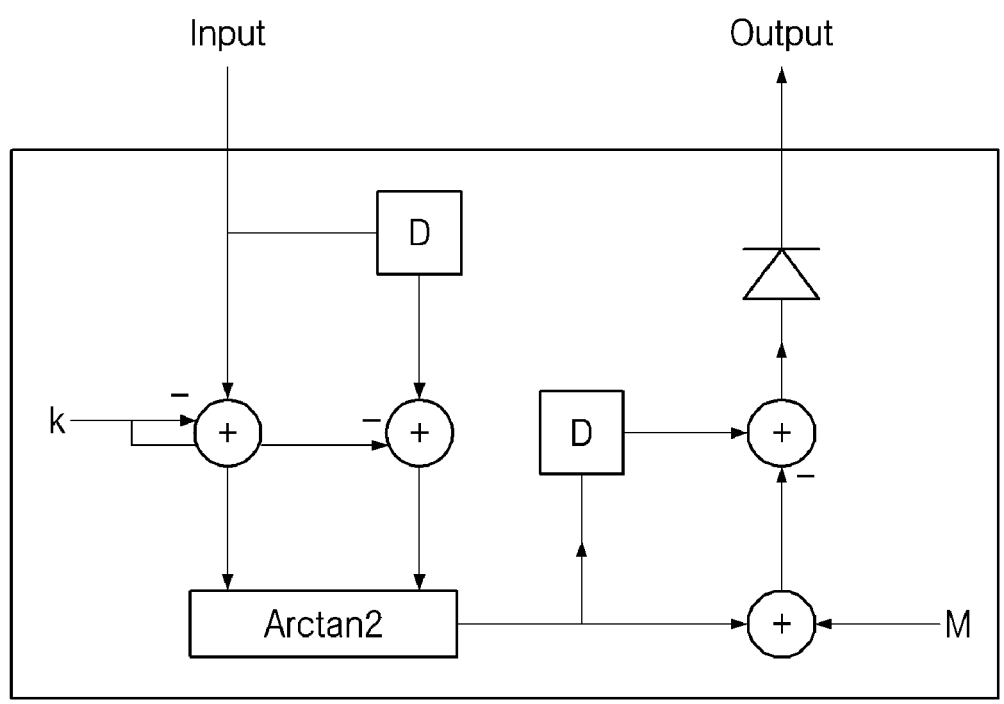
FIG. 7 is a diagram showing an embodiment in which the system for identifying a phase singularity according to an embodiment of the present invention has been implemented in an electronic circuit form.

Meanwhile, the system 100 for identifying a phase singularity according to an embodiment of the present invention may be implemented in the form of an electronic circuit not a device configuration, such as a system. The system may be implemented in various forms because it is an electronic circuit. One embodiment implemented in an electronic circuit form may be seen from FIG. 7.

Furthermore, the system 100 for identifying a phase singularity according to an embodiment of the present invention may be implemented as a method of identifying a phase singularity, including substantially the same characteristics as the system 100 for identifying a phase singularity according to an embodiment of the present invention, although they have different categories. This is described below with reference to FIG. 8.

Figure 8:
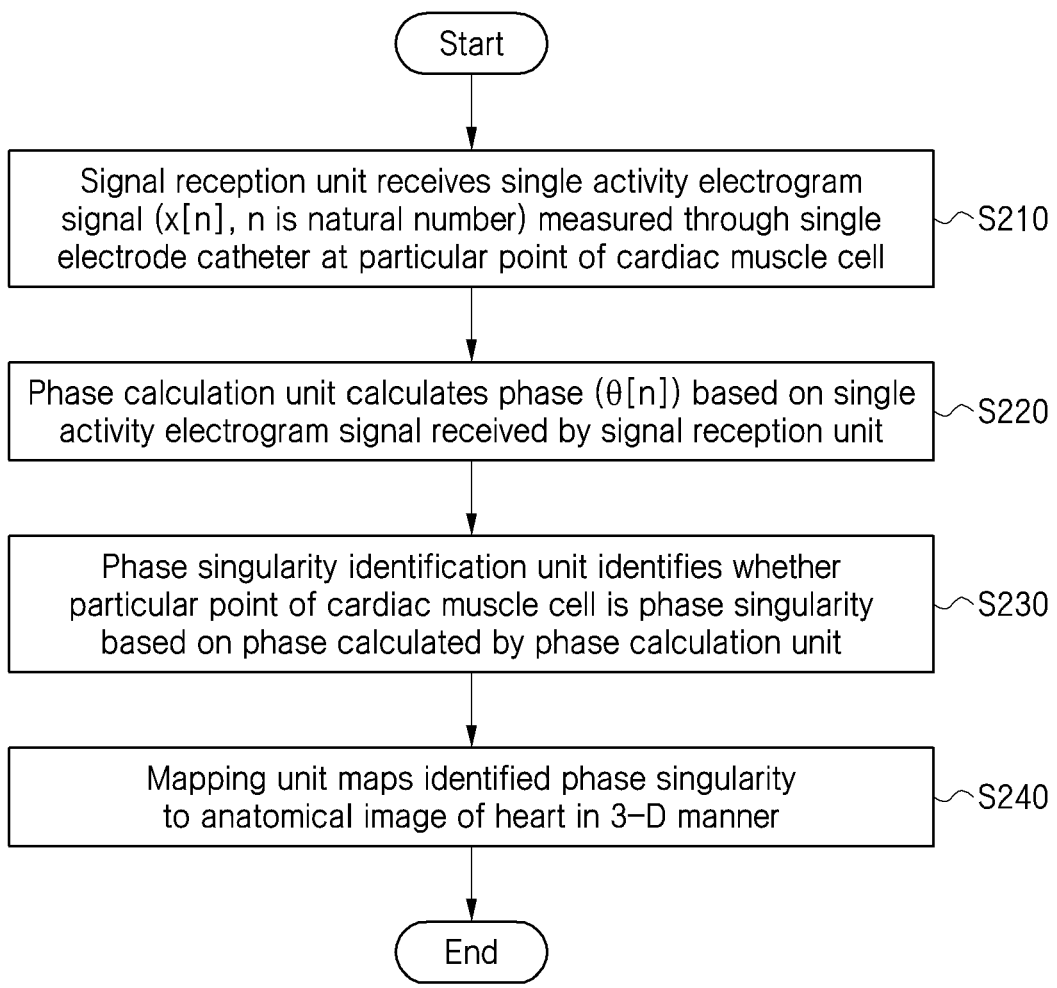
FIG. 8 is a diagram showing a flowchart of a method of identifying a phase singularity according to another embodiment of the present invention.

FIG. 8 is a diagram showing a flowchart of a method of identifying a phase singularity according to another embodiment of the present invention.

However, this is only the most preferred embodiment for achieving the object of the present invention, and some steps may be added or deleted.

First, the signal reception unit 10 receives a single activity electrogram signal ($x[n]$, n is a natural number) measured through a single electrode catheter at a particular point of a cardiac muscle cell (S210). In this case, a known electrode catheter used for a high-frequency electrode catheter ablation procedure may be used as the single electrode catheter. Unlike in a conventional technology using a multi-electrode catheter, the single activity electrogram of a point for identifying a phase singularity has only to be measured using a single electrode catheter. However, only one electrode catheter of a multi-electrode catheter may be used according to circumstances. Although only one electrode catheter of a multi-electrode catheter is used, the activity electrograms of points to surround a point for identifying a phase singularity do not need to be measured. Accordingly, the time taken to identify a phase singularity and a cost consumed therefor can be significantly reduced compared to a conventional technology.

Thereafter, the phase calculation unit 20 calculates a phase ($\theta[n]$) based on the single activity electrogram signal received by the signal reception unit 10 (S220). Specifically, the phase is calculated from the single activity electrogram signal according to [Equation 1] below.

$$\theta[n]=\arctan 2(x[n+\tau]-k, x[n]-k) \quad \text{[Equation 1]}$$

In this case, $\theta[n]$ is the phase, and $x[n]$ is the single activity electrogram signal. $\tau$ is a delay constant and may be set as a value corresponding a delay time, for example, 20 to 30 ms and may be freely adjusted by a system administrator. k is a base value of the single activity electrogram signal and may be set as the mean value of $x[n]$ or a specific constant, for example, 0. Like the delay constant, k may be freely adjusted by a system administrator.

Meanwhile, in the phase calculated according to [Equation 1], the electrical state of the cardiac muscle cell appears as values $-\pi$ to $+\pi$.

The phase calculation unit 20 calculates a phase $\theta[n+1]$ in addition to the phase $\theta[n]$ of $x[n]$, that is, a single activity electrogram signal, in order to perform the phase identification function of the phase singularity identification unit 30 (S221). In this case, the phase $\theta[n+1]$ may be calculated according to [Equation 1] below. A delay constant and a base value of the single activity electrogram signal needs to be set in the same manner as the case where the phase $\theta[n]$ is calculated. [Equation 2] may mean that the phase $\theta[n+1]$ is calculated according to [Equation 1].

$$\theta[n+1]=\arctan 2(x[n+1+\tau]-k, x[n+1]-k) \quad \text{[Equation 2]}$$

When the phase calculation unit 20 calculates the phase, the phase singularity identification unit 30 identifies whether a particular point of a cardiac muscle cell is a phase singularity based on the phase calculated by the phase calculation unit 20 (S230). Specifically, the phase singularity identification unit 30 identifies whether a particular point of a cardiac muscle cell is a phase singularity according to [Equation 3] below.

$$\theta[n+1]-\theta[n] \le -M \qquad \text{[Equation 3]}$$

In this case, M is a phase singularity identification condition and is theoretically $2\pi$, but may be set as a specific constant, for example, a constant such as $\pi$ by taking into consideration elements, such as noise in the measurement of a single activity electrogram signal.

If n to satisfy [Equation 3] is present, the phase singularity identification unit 30 identifies that the particular point of the cardiac muscle cell is a phase singularity. This is based on a physical fact that the phase $\theta[n]$ is continuous function at all of points of the cardiac muscle cell except a phase singularity. Specifically, in accordance with the definition of a phase singularity, a value not 0 is calculated when $\theta[n]$ is integrated in a path that surrounds the periphery of a phase singularity. The reason for this is that $\theta[n]$ is not mathematically a continuous function well defined in a single connection region.

When the phase singularity is identified, the mapping unit (not shown) maps the identified phase singularity to an anatomical image of the heart in a 3-D manner (S240). When the phase singularity is mapped to an anatomical image of the heart by the mapping unit (not shown), the high-frequency electrode catheter ablation procedure is connected to the system 100 for identifying a phase singularity. Accordingly, the mapped image may be received and easily used for a practical surgical procedure.

Although the present invention has not been described in detail in order to prevent redundant description, the characteristics described in relation to the system 100 for identifying a phase singularity may also be inferred and applied to the method of identifying a phase singularity. Furthermore, the method of identifying a phase singularity may be implemented in the form of a program stored in a medium and may be stored in a computer-readable recording medium in which a program for executing the method in a computer in this state is written or may be distributed through a program providing server. Moreover, if the method of identifying a phase singularity is implemented in a program form, the phase calculation unit 20 and the phase singularity identification unit 30 may be driven as independent threads to simultaneously process a plurality of single activity electrograms, thereby being capable of contributing to computing speed improvement.

The aforementioned embodiments of the present invention have been disclosed for illustrative purposes, and the present invention is not restricted by the embodiments. Furthermore, those skilled in the art to which the present invention pertains may modify and change the present invention in various ways within the spirit and range of the present invention, and such modifications and changes should be construed as belonging to the scope of the present invention.

INDUSTRIAL APPLICABILITY

The present invention has an advantage it can significantly reduce time and costs compared to a conventional method of identifying a phase singularity of a rotor in identifying the phase singularity of the rotor and thus has an industrial applicability.

The invention claimed is:

1. A system for identifying a phase singularity, comprising:
    a signal reception unit receiving a single activity electrogram signal (x[n], n being a natural number) measured through a catheter at a particular point of a cardiac muscle cell;
    a phase calculation unit calculating a phase ($\theta[n]$, n being a natural number in time unit) from the single activity electrogram signal received by the signal reception unit;
    a phase singularity identification unit identifying whether the particular point of the cardiac muscle cell is a phase singularity based on the phase calculated by the phase calculation unit; and
    a mapping unit mapping the identified phase singularity to an anatomical image of the heart in a three-dimensional manner,
    wherein the catheter includes only a single electrode,
    wherein the phase calculation unit calculates the phase up to $\theta[n+1]$ from the single activity electrogram signal received by the signal reception unit, and
    wherein the phase singularity identification unit identifies that the particular point of the cardiac muscle cell is a phase singularity using a phase difference between the calculated phase $\theta[n+1]$ and the calculated phase $\theta[n]$.

2. The system of claim 1, wherein the phase calculation unit calculates the phase from the single activity electrogram signal according to [Equation 1] below:

$$\theta[n]=\arctan 2(x[n+\tau]-k, x[n]-k) \qquad \text{[Equation 1]}$$

where $\theta[n]$ is the phase, x[n] is the single activity electrogram signal, $\tau$ is a delay constant, and k is a base value of the single activity electrogram signal.

3. The system of claim 1, wherein in the phase calculated by the phase calculation unit, an electrical state of the cardiac muscle cell appears as values $-\pi$ to $\pi$.

4. The system of claim 1, wherein the phase singularity identification unit identifies that the particular point of the cardiac muscle cell is a phase singularity when n satisfying [Equation 3] below is present:

$$\theta[n+1]-\theta[n] \le -M \qquad \text{[Equation 3]}$$

where M is a phase singularity identification condition and is a specific constant.

5. The system of claim 4, wherein M which is the phase singularity identification condition is $\pi$.

6. A method of identifying a phase singularity, comprising steps of:
    (a) receiving, by a signal reception unit, a single activity electrogram signal (x[n], n being a natural number) measured through a catheter at a particular point of a cardiac muscle cell;
    (b) calculating, by a phase calculation unit, a phase (O[n], n being a natural number in time unit) from the single activity electrogram signal received by the signal reception unit;
    (c) identifying, by a phase singularity identification unit, whether the particular point of the cardiac muscle cell is a phase singularity based on the phase calculated by the phase calculation unit, and
    (d) mapping, by a mapping unit, the identified phase singularity to an anatomical image of the heart in a three-dimensional manner, wherein the catheter includes only a single electrode, wherein the phase calculation unit calculates the phase up to θ[n+1] from the single activity electrogram signal received by the signal reception unit, and wherein the phase singularity identification unit identifies that the particular point of the cardiac muscle cell is a phase singularity using a phase difference between the calculated phase θ[n+1] and the calculated phase θ[n].

7. The method of claim 6, wherein the step (b) comprises calculating the phase from the single activity electrogram signal according to [Equation 1] below:

$$\theta[n] = \arctan 2(x[n+\tau]-k, x[n]-k) \quad \text{[Equation 1]}$$

where θ[n] is the phase, x[n] is the single activity electrogram signal, τ is a delay constant, and k is a base value of the single activity electrogram signal.

8. The method of claim 6, wherein in the phase calculated in the step (b), an electrical state of the cardiac muscle cell appears as values $-\pi$ to $\pi$.

9. The method of claim 6, wherein the step (c) comprises (c-1) identifying that the particular point of the cardiac muscle cell is a phase singularity when n satisfying [Equation 3] below is present:

$$\theta[n+1] - \theta[n] \leq -M \quad \text{[Equation 3]}$$

where M is a phase singularity identification condition and is a specific constant.

10. The method of claim 9, wherein the M is $\pi$.

11. A program stored in a non-transitory storage medium for executing the method of claim 6 in a computer.

12. A program stored in a non-transitory storage medium for executing the method of claim 7 in a computer.

13. A program stored in a non-transitory storage medium for executing the method of claim 8 in a computer.

14. A program stored in a non-transitory storage medium for executing the method of claim 9 in a computer.

15. A program stored in a non-transitory storage medium for executing the method of claim 10 in a computer.

* * * * *